US006245096B1

(12) United States Patent
Tomic-Edgar et al.

(10) Patent No.: US 6,245,096 B1
(45) Date of Patent: Jun. 12, 2001

(54) THERMAL COVER MEMBER FOR DELIVERING FLUID TO A PATIENT

(75) Inventors: Kerry Tomic-Edgar, Santa Ana; Gordon Y. Shigezawa, Irvine; Anthony V. Beran, Santa Ana, all of CA (US)

(73) Assignee: Respiratory Support Products, Inc., Irvine, CA (US)

(*) Notice: Subject to any disclaimer, the term of this patent is extended or adjusted under 35 U.S.C. 154(b) by 0 days.

(21) Appl. No.: 09/385,827

(22) Filed: Aug. 30, 1999

(51) Int. Cl.$^7$ ........................................... A61F 7/00
(52) U.S. Cl. ............................. 607/107; 607/104
(58) Field of Search .............. 607/96, 104, 107, 607/114

(56) References Cited

U.S. PATENT DOCUMENTS

| | | | |
|---|---|---|---|
| 4,325,254 | * 4/1982 | Svacina et al. | 73/356 |
| 4,846,176 | * 7/1989 | Golden | 128/400 |
| 5,300,102 | * 4/1994 | Augustine et al. | 607/107 |
| 5,366,491 | * 11/1994 | Ingram et al. | 607/108 |
| 5,640,728 | * 6/1997 | Graebe | 5/606 |
| 5,954,680 | * 9/1999 | Augustine | 602/42 |
| 5,968,084 | * 10/1999 | Augustine et al. | 607/107 |
| 5,989,285 | * 11/1999 | DeVilbiss et al. | 607/107 |

* cited by examiner

*Primary Examiner*—Linda C. M. Dvorak
*Assistant Examiner*—Jocelyn Debra Ram
(74) *Attorney, Agent, or Firm*—Price and Gess (57) ABSTRACT

A thermal cover member for delivering a fluid to a patient's body, such as heated or cooled air, includes a hollow housing member having an inlet port for receiving the pressurized fluid. A plurality of cells are positioned about the housing member to create fluidic spaces for applying the fluid to the body of the patient. Each cell has a non-inflatable canopy with a continuous perimeter sealingly connected to the housing member with the housing member having a plurality of exit ports communicating with each cell to provide an egress of fluid. The fluidic spaces within a cell can be dimensioned to accommodate anatomical configurations of the patient's body and a thermo-chromatic indicator can be provided on the cover member to indicate a temperature of the corresponding fluidic space. The canopy can be transparent to permit viewing of the patient's body.

41 Claims, 4 Drawing Sheets

THERMAL COVER MEMBER FOR DELIVERING FLUID TO A PATIENT

BACKGROUND OF THE INVENTION

1. Field of the Invention

The present invention is directed to a thermal cover member for delivering a fluid such as air to a patient's body and more particularly for providing a plurality of cells that form fluidic spaces across the patient's body while optionally providing the ability to visually monitor the temperature and the patient skin response under the fluidic spaces.

2. Description of Related Art

The prior art has long recognized the desirability of providing convective fluid flow to a person's body to either warm or cool the person's body. Various delivery systems have been utilized, including porous mattresses and inflatable blankets that are connected to a pressurized source of fluid. For example, U.S. Pat. No. 2,093,834 discloses providing fabric material formed by a plurality of layers sewed together so that air-conditioned air could be diffused through the layers to come into contact with the body of the person. This reference also teaches the use of body suits and the application of both cooled and heated air that is supplied under pressure to a flexible enclosure. U.S. Pat. No. 2,601,189 teaches an air comforter bed covering that can be formed of thermally bonded plastic material.

U.S. Pat. No. 3,757,366 teaches providing heated air through a cushion device that can be positioned beneath the body of the user. U.S. Pat. No. 3,778,851 is an example of a mattress that could be used for treating a patient who has undergone surgery, or is recovering from severe burns. A series of welded seams can divide the mattress into rib conduits that communicate with a peripheral manifold. Apertures in the ribs permit the egress of air, while supplemental resilient foam plastic material can be positioned within the ribs and a manifold.

U.S. Pat. No. 3,881,477 discloses a rectangular hollow tubular structure that is positioned above a patient to deliver a stream or curtain of air in upper and downward directions to create a super-atmospheric pressure zone about the patient's body for a surgical field so that it is isolated from outside air and airborne foreign particles.

U.S. Pat. No. 3,908,655 discloses a post-operative cooling device that can encompass the head and neck of a patient.

The following patents have attempted to provide various structures of thermal blankets, such as U.S. Pat. Nos. 5,324,320, 5,300,102, 4,572,188, 4,777,802, 5,350,417, 5,125,238 and 5,405,271.

The medical profession has been well aware of postoperative hypothermia that can be experienced by a significant number of patients that have undergone surgery. The art is still seeking to optimize a relatively inexpensive and disposable device to address these issues, plus providing an option of easily monitoring the temperature of fluid applied to the patent.

SUMMARY OF THE INVENTION

The present invention provides a thermal cover member for delivering a fluid, such as heated or cooled air, to a patient's body. The cover member includes a hollow housing member having an inlet port for connection with a source of pressurized fluid, such as an air heater. The hollow housing member can include a first flexible member and a second flexible member connected together to provide a manifold conduit with a plurality of cells positioned about the housing member to create fluidic spaces or zones. The manifold conduit is expandable when pressurized by the fluid. Each cell includes a non-inflatable canopy that has a continuous perimeter sealingly connected to the housing member or manifold conduit. The housing member can have a plurality of exit ports communicating with each cell to provide an egress of fluid to create a fluidic space in each cell beneath each canopy to bathe a portion of the patient's body with fluid for temperature control purposes. The cells can be dimensioned to accommodate anatomical characteristics of a particular patient by size and sex. The exit ports on the perimeter side walls of the cell, that are part of the manifold conduit, can direct egressing fluid into the interior of the fluidic spaces to provide a controlled temperature zone to the body of the patient. The first flexible member and the second flexible member preferably includes plastic and can be heat-welded together to form continuous, seam-sealed connections about each canopy. The canopy can also support a thermo-chromatic indicator to visually indicate the temperature of the fluidic space in each cell and/or can include a transparent window to enable a visual monitoring of the patient's skin.

Preferably, a cover member for delivering fluid to the patient, is a disposable flexible body member that can expand to provide a manifold conduit for delivery of fluid to the patient. A thermo-chromatic detector can be operatively connected to this cover member for providing a visible indicator of the temperature of the fluid.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may be best understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a thermal cover member for controlling the application of a fluid to specific areas of a patient's body.

Figure 1:
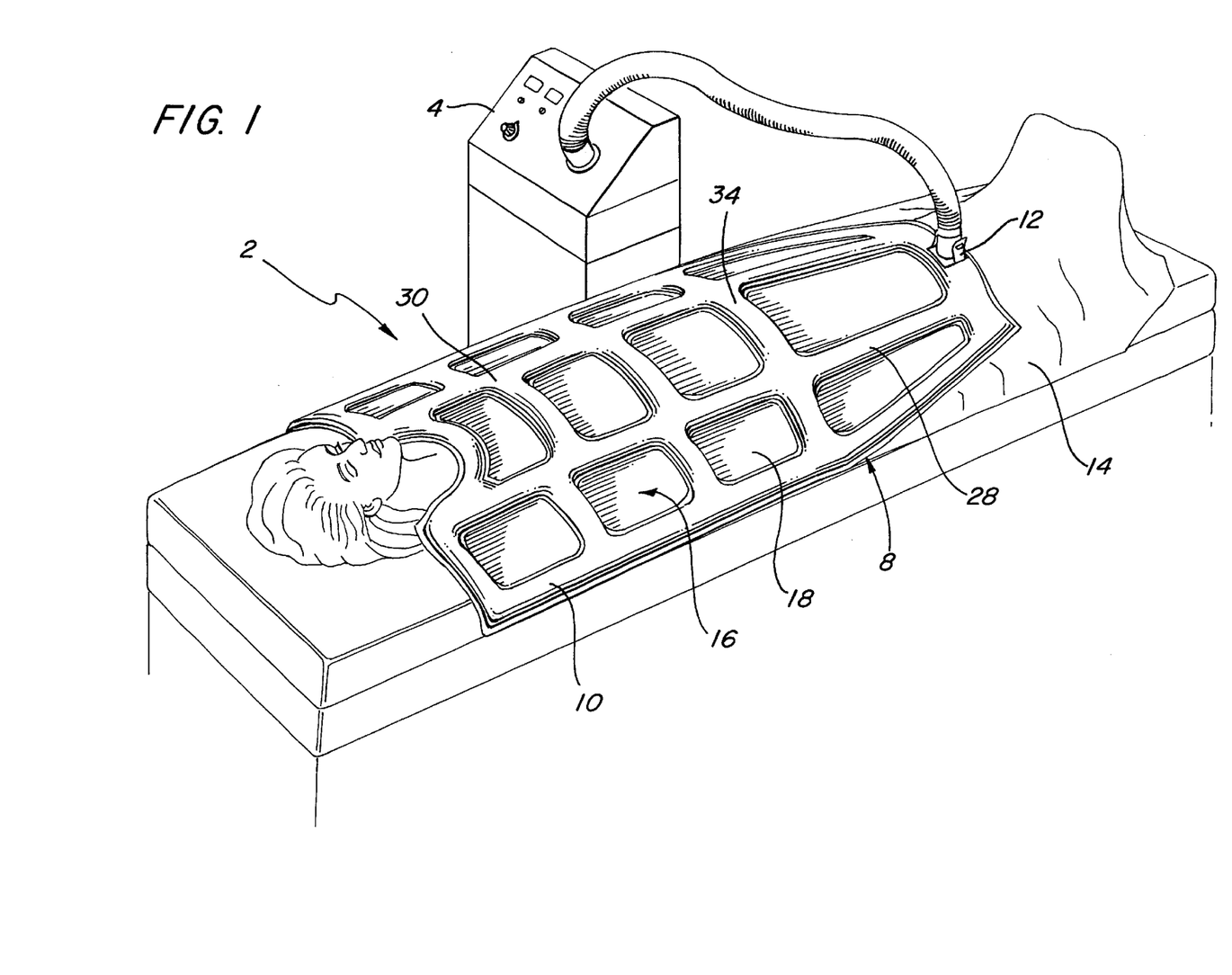
FIG. 1 provides a perspective view of a thermal cover member of the present invention as applied to a patient.

Referring to FIG. 1, a thermal cover member 2 of the present invention is disclosed in a post-operative situation covering a patient's body. The cover member 2 is disclosed in an inflated condition of being pressurized by a fluid, such as heated air from a hot air heater 4 that is connected to the cover member 2 by a flexible conduit 6. A hot air heater such as disclosed in U.S. Pat. No. 5,785,723 and incorporated herein by reference can be used. While a hot air heater 4 is disclosed, it is also possible to use an air cooler, alternative sources of fluid, such as an oxygen-rich gas for burn victims, and/or an air sterilizer for specific treatment to the patient with the same cover member of the present invention. Additional medicinal vapors can be optionally added to the fluid. When a patient is being treated to prevent hypothermia, a hot air flow usually within a temperature range of 36° to 42° C. is provided to the cover member 2. The cover member 2 is inflated as a result of the pressurized air providing a pressure of 1.5 centimeters of water with a delivery rate of 60 cubic feet of air per minute. An inlet port 12 can be detachably connected to a nozzle of the flexible conduit 6 in a conventional manner to supply the pressurized air.

The thermal cover member 2 includes a hollow housing member, or manifold conduit 8. A portion of the manifold conduit 8 surrounds or encircles a periphery of the hollow housing member as a peripheral manifold conduit 10. Intermediate manifold conduits can extend longitudinally and traversely between the peripheral manifold conduit 10 to help define temperature zones above the patient's body.

In the embodiment of FIG. 1, a cover flap 14 extends from the lower end of the thermal cover member 2 to cover the patient's feet. The cover flap 14 can be a non-inflatable extension of the thermal cover member 2. The end of the thermal cover member 2, proximal the head of the patient, has an appropriate indent to accommodate the patient's neck and head.

Figure 2:
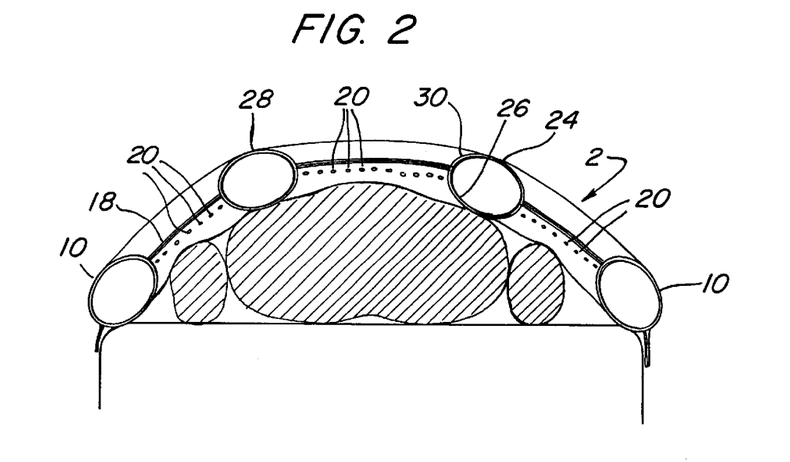
FIG. 2 is a cross sectional schematic view of a thermal cover member of FIG. 1.
Figure 3:
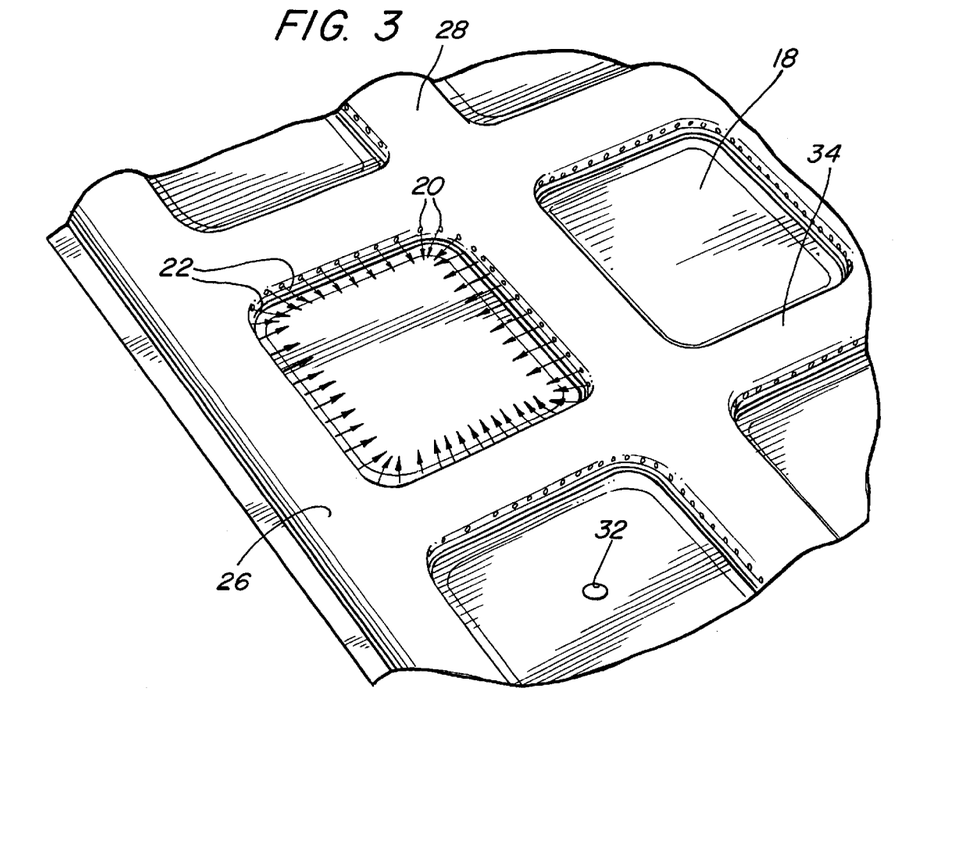
FIG. 3 is a partial perspective view of the underside of thermal cover member of FIG. 1.

As can be seen in FIGS. 1 and 3, a matrix of cells 16 of different sizes are positioned across and about the housing member. Each cell 16 includes a non-inflatable canopy 18 with a continuous seam perimeter sealingly connected to the housing member or manifold conduit 8. The particular configuration and size of the canopy and the corresponding cells can be subjectively arranged to accommodate the anatomical features of the human body. For example, a female patient with breasts could have an appropriate cell arranged to deliver heated air in a fluidic space beneath the canopy of that cell to her chest. The periphery of each cell is further formed by the interior walls of the manifold conduit 8 and is fluid permeable to permit an egress of fluid into each fluidic space beneath a canopy. As shown in FIGS. 2 and 3, a series of perforations or holes 20 can surround a continuous seam-sealed perimeter 22. The holes are positioned on the sides and not the bottom of the interior walls and direct the fluid in streams that are approximately parallel to the canopy for mixing in the cell. By providing the holes on the sides instead of the bottom, those holes will not be blocked by contacting the patient's body. Thus, a more controlled back pressure will be experienced with an even distribution of fluid.

The cover member has a flexible body member that can be formed from a first flexible member 24 and a second flexible member 26. The flexible body member, when not subject to fluid pressure, resembles a flat, two-ply sheet configuration. The first flexible member 24 and the second flexible member 26 can be formed from a spun-bound polypropylene sheet coated with a 0.5 mil of a low density polyethylene. The sheets are liquid-proof and have a weight of approximately one ounce per square yard. The polyethylene coated sides of the respective first flexible member 24 and second flexible member 26 are positioned to overlay each other and during manufacturing an application of heat by a platen (not shown) can define an outer continuous sealed-seam perimeter of the hollow housing member, and also interior, continuous sealed-seam perimeter of the individual sizes of the plurality of cells positioned about the housing member. Each cell 16 can have a continuous sealed perimeter seam that is heat-sealed together. Perforations in the lower or second flexible member 26 adjacent the continuous sealed seam perimeter 22, shown in FIG. 3, provide egress for pressurized fluid to flow into the cells. By varying the size of the perforations 20, for example if the perforations are circular then by varying the diameter of the hole, the amount of fluid flow into a cell can be controlled. Alternative forms of other material, such as paper and plastic can be used. In one embodiment of the present invention shown in FIG. 6, transparent sheets of plastic can be used to permit an observation of the patient's skin.

Referring to FIG. 2, a cross sectional view of the thermal cover member 2 is shown in an inflated state. Respective first flexible member 24 and second flexible member 26 are expanded by the pressurized fluid so that the peripheral manifold conduit 10 and intermediate longitudinal conduits 28 and 30 are expanded. The canopies 18 that form the top of each cell 16 do not expand since the continuous sealed perimeter 22 around each cell 16 isolates the canopies 18 and leaves them in a flat relatively planar configuration in an intermediate position between the conduits. If these canopies 18 are transparent, it is easy to maintain a visual monitoring of the patient's body. By providing an intermediate position for the canopy, manufacturing is facilitated, however the canopy can be raised or lowered, depending on the desired volume of the fluidic space. The individual cells 16 define fluidic spaces in the cavity beneath each cell and they are bounded by the sealed continuous seam perimeter 22, the canopy 18, and depending upon the position of a 16 cell within the matrix of the hollow housing member, the fluidic space is bounded by either a peripheral conduit 10 and a longitudinal conduit or a pair of longitudinal conduits while the other two sides of the cell are formed by traverse conduits such as conduits 34. The longitudinal conduits, traverse conduits and peripheral conduits collectively can provide a manifold conduit for providing fluid to the respective perforations 20 defined about the perimeter of each cell 16. The perforations 20 in a preferred embodiment are positioned in the respective conduits and adjacent the sealed continuous seam perimeter of a cell so that a fluid, such as air is directed inward and approximately parallel to the undersurface of the canopy 18. As shown in FIG. 3, perforations can extend about all four sides of the conduit walls forming a portion of the fluidic space. As can be appreciated, it is possible to provide perforations on less than all four sides, as long as an adequate flow of fluid is being provided to the cavity space. As can be seen in FIG. 2, partial sections of three separate cavity spaces are positioned across a patient's body and as can be readily appreciated the body is only contacted by the lower surface of the manifold conduit 8.

In the full body cover member of the embodiment of the invention shown in FIG. 1, the total surface area of the manifold conduit including the canopies can, for example, be 2,265 square inches, while the canopy surface area will constitute 872 square inches. These area dimensions do not include the non-inflated flat cover section 14, thus the canopy area which defines the area of the fluidic space represents greater than 30% and less than 38% of the surface area supporting and providing fluid to the patient's body. The twelve fluidic spaces defined by the canopies shown in the embodiment of FIG. 1 have approximate surface areas varying from 50 square inches to 144 square inches.

Needless to say, variations from these dimensions can be accomplished and thermal cover members of various sizes can be designed for adults, children and pediatric use. For example, an alternative embodiment could first cover the upper body and arms of a patient. Additionally, as known, adhesive tape can be used for securement to a patient.

As shown in FIG. 3, a hole 32 can be provided either during the manufacturing of the thermal cover member or can be subsequently cut into a canopy 18 to assist in increasing the flow of fluid into a specific cell so that the fluidic space can increase the fluid flow and accordingly the delivery of heat to a selected portion of the patient's body. When the pressurized fluid is delivered through the perforations into a particular cell, a back pressure of resistance is incurred and by providing an orifice or hole 32 in the canopy, the fluid such as air will be released from the fluidic space thereby lowering the back pressure and increasing the air flow into a particular cell.

Figure 4:
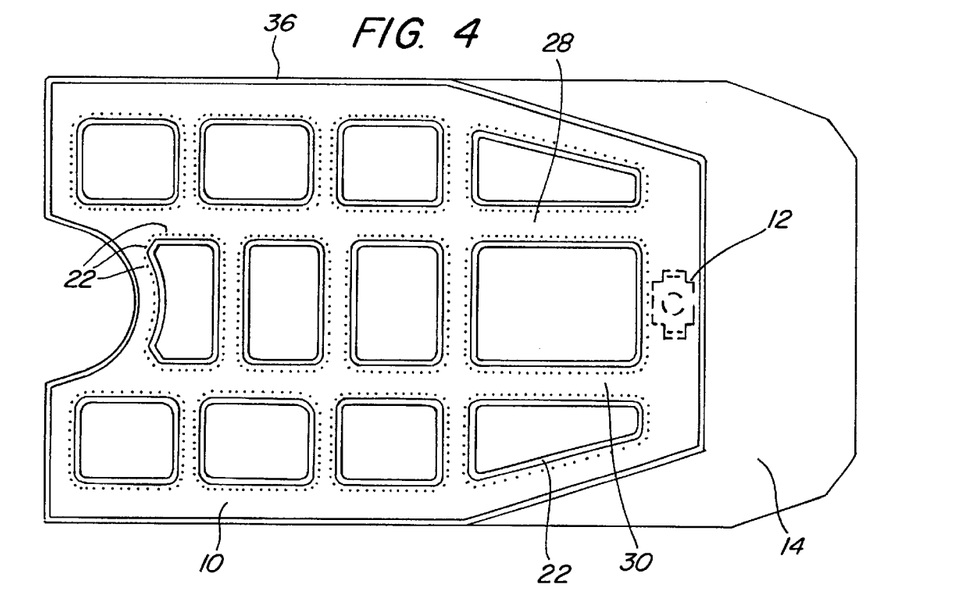
FIG. 4 is an uninflated plane bottom view of the thermal cover of FIG. 1.

Referring to FIG. 4, a bottom plan view is disclosed for the thermal cover member 2 of FIG. 1. This thermal cover member 2 is a full body blanket adult cover and extends approximately 80 inches in length and 40 inches in width. These dimensions include the approximately 15 inches in length of the flap cover 14. The peripheral conduit 10 is somewhat larger in size or diameter than the respective longitudinal conduits and traverse conduits that collectively form the manifold conduit 8. As can be seen, a heat sealed continuous perimeter seam 36 defines the outer perimeter of the manifold conduit 8. The matrix of cells 16 each have internal continuous perimeter seams 22 that define the outer perimeter of each of the non-inflatable canopies 18.

Figure 5:
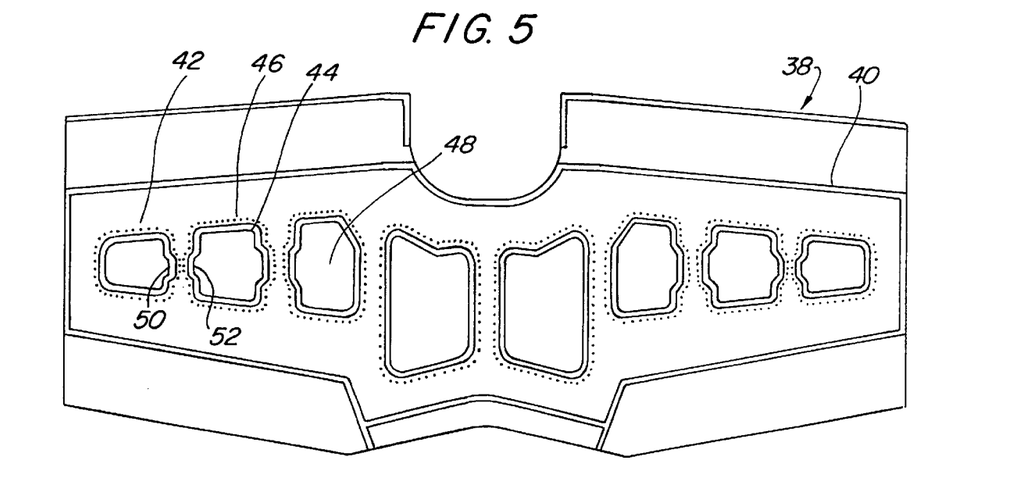
FIG. 5 is an uninflated plane bottom view of an alternative embodiment.

Another embodiment of a thermal cover member of the present invention is shown in a bottom plane view of FIG. 5. This embodiment is an upper adult body cover member 38 with eight cells that are designed to extend over the outstretched arms and chest of the patient. This upper body thermal cover 38 has an outer perimeter continuous seal 40 and a series of aligned cells 42, each with a continuous internal heat-welded seal 44. Appropriate perforations 46 are provided about the perimeter of each cell adjacent the respective canopies 48 and below the continuous seam. To further accommodate the configuration of the appendages of the patient, which in this case is the outstretched arms of the patient, the longitudinal conduits that extend between respective cells can be configured to further conform to the anatomical configuration of the arms. Thus, as seen in FIG. 5 the continuous heated welded seam 44 can have concave portions 50, 52 on adjacent continuous heat welded seams to provide an elevated position of the manifold and to thereby permit an easier compliance with the appendage. As can be readily appreciated, the configuration of the cells can be further modified, depending upon the particular application of the thermal cover and the portion of the body for the patient that is to be supplied with a fluid.

Figure 6:
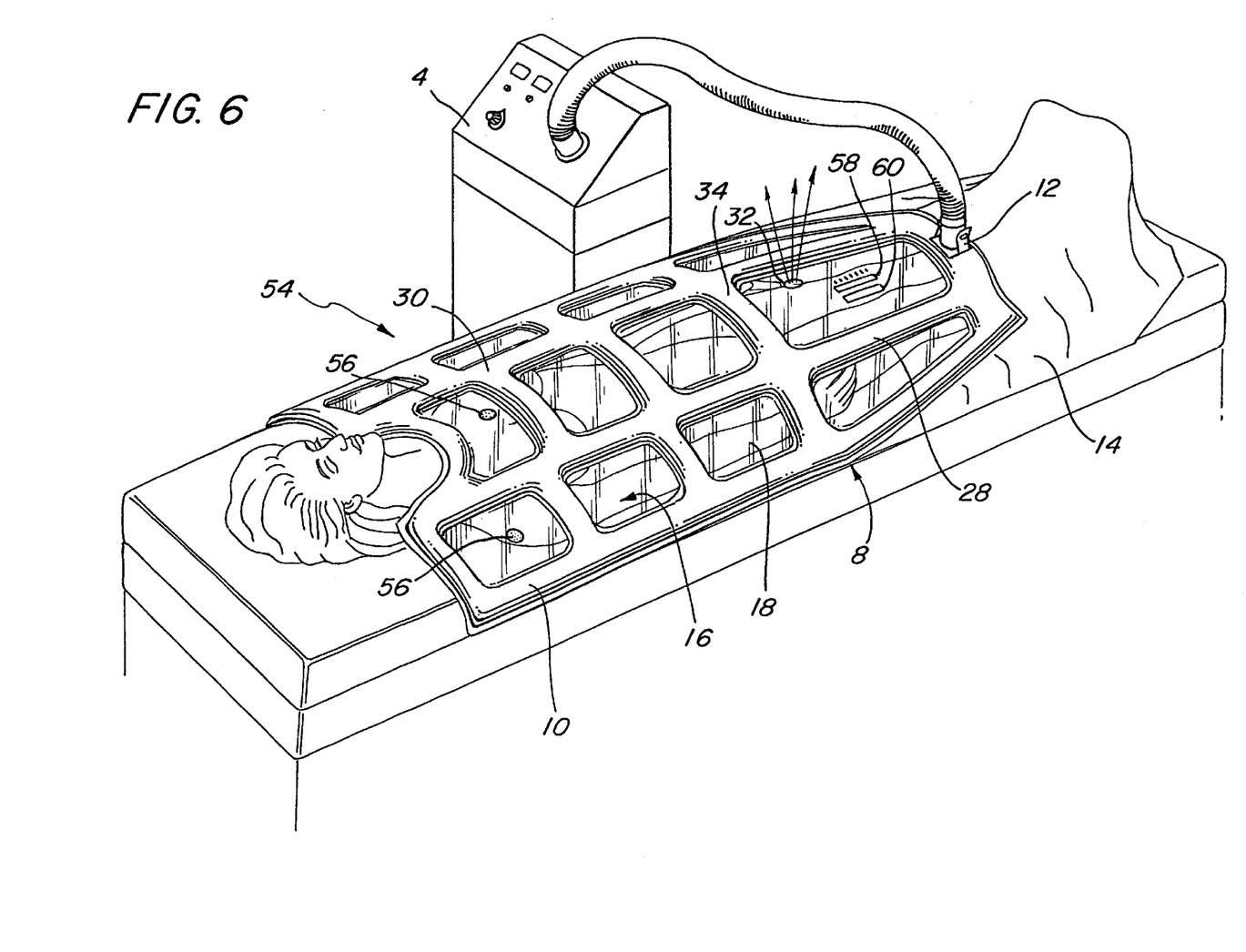
FIG. 6 is a perspective view of a thermal cover member with a thermo-chromatic indicator and transparent windows.

Referring to FIG. 6, a modified cover member 54 of the present invention is provided with visual temperature indicators 56, indicating the respective temperatures of cells on the hollow housing member. These thermo-chromatic indicators 56 can be attached, for example, to a canopy and can include a temperature responsive member, such as a liquid crystal diode material that has the capacity to change color to measure a particular temperature within our operative temperature range.

Alternatively, the thermo-chromatic material that is used to form the indicators can also be chosen from various polymer compositions in the form of printing ink, thermo-chromatic paints, thermo-chromatic sheets and encapsulated thermo-chromatic materials. For background on thermo-chromatic material of this type, reference can be made to U.S. Pat. No. 4,028,118, which is incorporated herein. Basically the thermo-chromatic material should be non-toxic and exhibit a sharp, reversible metachromatism at selected temperatures that are within the operative temperature range of our thermal cover. It is also possible to provide a scale or indicator adjacent the temperature sensitive thermo-chromatic material so that a particular temperature can be identified or matched with the scale. For example, a scale or reference strip 58 can be appropriate color-coded with even temperature indicia printed on the canopy adjacent a thermo-chromatic indicator 60. When the temperature sensed by the thermo-chromatic indicator 60 produces an appropriate color change, the observer can correlate that color change with the scale 58.

As can be appreciated, by providing these passive thermo-chromatic indicators on each of the canopies forming the respective cells, the monitoring medical personnel can visually identify the heat flow to particular locations of the patient's body since the fluid flow to a fluidic space formed within a cell will affect the temperature of the canopy and accordingly, the temperature of the thermo-chromatic indicator 56. Additionally, by providing an opening in a canopy, for example the medical personnel can cut a port 32 into a canopy, heat flow can be increased to a particular cell, as shown in FIG. 6 and monitored by the indicator 60.

Finally, as shown in FIG. 6, the canopies above each cell can be transparent to permit visual observation of the body. The transparent canopies can be formed by having a transparent upper flexible member and cutting the lower flexible member before heat sealing. Alternately, the upper and lower flexible members can be cut and a transparent plastic canopy can be sealed over each cell.

Those skilled in the art will appreciate that various adaptations and modifications of the just-described preferred embodiments can be configured without departing from the scope and spirit of the invention. Therefore, it is to be understood that within the scope of the appended claims, the invention may be practiced other than as specifically described herein.

What is claimed is:

1. A thermal cover member for delivering a fluid to a patient's body comprising:
   a hollow housing member having an inlet port for receiving a pressurized fluid; and
   a plurality of cells positioned about the housing member, each cell has a non-inflatable canopy that has a continuous perimeter sealingly connected to the housing member, the housing member has a plurality of exit ports communicating with each cell to provide an egress of fluid to create a separate fluidic space in each cell beneath each canopy to deliver fluid to the patient's body through each fluidic space.

2. The thermal cover member of claim 1 wherein the fluidic space in each cell is dimensioned to accommodate anatomical configurations of the patient's body.

3. The thermal cover member of claim 1 wherein a thermo-chromatic indicator is provided on the cover member to indicate a temperature.

4. The thermal cover member of claim 3 wherein the thermo-chromatic indicator includes a portion of the canopy covered with a thermo-chromatic material.

5. The thermal cover member of claim 1 wherein a plurality of thermo-chromatic indicators are positioned on a plurality of canopies to indicate temperatures associated with corresponding fluidic spaces.

6. The thermal cover member of claim 4 wherein the thermo-chromatic material is configured to provide indicia indicative of a desired temperature level when the fluidic space reaches a pre-determined temperature.

7. The thermal cover member of claim 1 wherein the total surface area of the cell canopies is greater than 30 percent of the total surface area of the hollow housing member and the cell canopies.

8. The thermal cover member of claim 3 wherein the thermo-chromatic indicator includes a portion of the canopy supporting a liquid-crystal material that changes color corresponding to a temperature.

9. The thermal cover member of claim 1 wherein the hollow housing member is approximately flat and upon receiving a pressurized fluid is inflated to provide a fluidic manifold to supply fluid to each cell.

10. The thermal cover member of claim 9 wherein the hollow housing member has a periphery fluid channel that is larger in cross section than internal fluid channels between the cells.

11. The thermal cover member of claim 9 wherein at least ten cells are positioned about the housing member.

12. The thermal cover member of claim 11 wherein an area of the canopy of each cell is at least forty square inches.

13. The thermal cover member of claim 1 wherein certain of the plurality of cells are aligned to enable an alignment of a portion of the cover member across an appendage of a patient and intermediate portions of the hollow housing member between the aligned cells are reduced in size and configured to accommodate the appendage and minimize relative movement.

14. The thermal cover member of claim 1 wherein the hollow housing member that encircles about the periphery of a canopy is fluid permeable and directs the fluid in a direction approximately parallel to a plane containing the canopy.

15. The thermal cover member of claim 1 wherein the hollow housing member comprises a first flexible member and a second flexible member, wherein the second flexible member is connected to the first flexible member, to provide a manifold conduit wherein the first flexible member and the second flexible member define an inflatable space at positions offset from a peripheral connection and a continuous seam connection about each canopy.

16. The thermal cover member of claim 15 wherein the canopy is formed of the first flexible member overlapping the second flexible member.

17. The thermal cover member of claim 16 wherein the portion of the hollow housing member that encircles about the periphery of a canopy has a plurality of perforations.

18. The thermal cover member of claim 17 wherein the plurality of perforations about the periphery of one canopy has larger openings than the size of the plurality of perforations about the periphery of another canopy.

19. The thermal cover member of claim 1 wherein at least one canopy has an opening to permit the egress of fluid from the cell fluidic space to increase fluid flow into the cell.

20. The thermal cover member of claim 15 wherein the first flexible member and the second flexible member are at least a two-ply composition of a plastic sheet and a plastic coating, the flexible members are heat-welded together to form continuous seam connection about each canopy.

21. The thermal cover member of claim 1 wherein at least one canopy is transparent to permit viewing the patient's body beneath the canopy.

22. A cover member for delivering a fluid to a body of a patient, comprising:
a flexible body member including a conduit for the fluid and a plurality of cells communicating with the conduit to provide an egress of fluid from the conduit to create a fluidic space in each cell above the body of the patient whereby a different heat flow can be provided to different portions of the patient's body from one fluidic space to another.

23. The cover member of claim 22 wherein the conduit encircles more than one cell and is fluid permeable about a periphery of the cell.

24. The cover member of claim 23 wherein each cell is formed of a sheet member extending between a perimeter bounded by the conduit.

25. The cover member of claim 24 wherein the conduit is inflatable by the fluid when delivered under pressure to suspend the sheet member above the body of the patient and to create a fluidic space beneath the sheet member.

26. The cover member of claim 25 wherein the sheet member is substantially planar.

27. The cover member of claim 22 wherein the cell is transparent to permit viewing of the patient's body.

28. The cover member for delivering fluid to a patient comprising:
a flexible body member including a first flexible member and a second flexible member, wherein the second flexible member is connected to the first flexible member to provide a conduit for delivering of fluid; and
a plurality of cells formed in the flexible body member, each cell provides a fluidic space above the patient when the conduit contacts the patient, the conduit further permits an egress of fluid into each fluidic space.

29. A cover member for delivering fluid to a body of a patient comprising:
a flexible body member including a manifold conduit for the fluid and a plurality of cells communicating with the manifold conduit to provide an egress of fluid from the conduit to create a fluidic space in each cell above the body of the patient, and
a thermo-chromatic material, providing a visible and reversible meta-chromatism at an operative temperature range for delivered fluid, on the flexible body member whereby the temperature of the fluidic space can be monitored.

30. The cover member of claim 29 wherein the conduit encircles at least more than one cell and is fluid permeable about a periphery of each cell.

31. The cover member of claim 30 wherein a cell includes a canopy sheet member extending between a perimeter bounded by the conduit.

32. The cover member of claim 31 wherein thermo-chromic material is positioned on two or more canopy sheet members for respectively monitoring the temperature of corresponding fluid space.

33. The cover member of claim 32 wherein the conduit is inflatable by the fluid when delivered under pressure to suspend the canopy sheet member above the body of the patient and to create a fluidic space beneath the canopy sheet member.

34. A cover member for delivering fluid to a patient comprising:
a flexible body member including a first flexible member and a second flexible member, connected to the first flexible member to provide a conduit for delivery of fluid, a portion of one of the flexible members is porous to permit an egress of fluid to the patient; and a thermo-chromic detector operatively printed on the cover member for providing a visible indicator of the temperature of the fluid.

35. A thermal cover member for contacting and delivering air to a patient's body comprising:
    a hollow housing member having an inlet port for receiving pressurized air, the housing member including a peripheral conduit having a plurality of longitudinal and traverse conduits extending within and between the peripheral conduit; and
    a plurality of cells integrally positioned about the housing member and formed between the conduits, each cell has a non-inflatable canopy that has a continuous perimeter sealingly connected to the housing member, the housing member has a plurality of exit ports communicating with each cell to provide an egress of air to create a fluidic space in each cell beneath each canopy to define separate zones for delivery of air to the patient's body as the thermal cover member is maintained in contact with and over the patient's body.

36. The thermal cover member of claim 35 wherein a thermo-chromatic indicator is provided on at least one of the canopies to indicate a temperature.

37. The thermal cover member of claim 36 wherein the peripheral conduit is larger in cross-section than the longitudinal and traverse conduits.

38. The thermal cover member of claim 37 wherein the plurality of perforations about the periphery of one canopy have larger openings than the size of the plurality of perforations about the periphery of another canopy.

39. The thermal cover member of claim 35 wherein a plurality of thermo chromatic indicators are positioned separately on a plurality of canopies to indicate temperatures associated with corresponding fluidic spaces beneath each canopy.

40. The thermal cover member of claim 35 further including means for varying the volume of air flow to each fluidic space whereby the separate temperature zones beneath each canopy are provided.

41. The thermal cover of claim 40, wherein the means for varying includes the plurality of exit ports communicating with one cell has larger openings than the size of the plurality of exit ports communicating with another cell.

* * * * *

UNITED STATES PATENT AND TRADEMARK OFFICE
CERTIFICATE OF CORRECTION

PATENT NO. : 6,245,096 B1  
DATED : June 12, 2001  
INVENTOR(S) : Kerry Tomic-Edgar et al.

Page 1 of 1

It is certified that error appears in the above-identified patent and that said Letters Patent is hereby corrected as shown below:

<u>Title page,</u>
Please list the following U.S. Patents under the References Cited section, of Patent No. 6,245,096.
1,777,982 - 01/07/30 - Popp
2,110,022 - 03/01/38 - Kilierrath
2,093,834 - 09/21/37 - Gaugler
2,601,189 - 06/17/52 - Wales, Jr.
3,757,366 - 09/11/73 - Sacher
3,778,851 - 12/18/73 - Howoarth
3,881,477 - 05/06/75 - Von Otto
3,908,655 - 09/30/75 - Lund
4,028,118 - 06/07/77 - Nakasuji, et al.
4,572,188 - 02/25/86 - Augustine, et al.
4,777,802 - 10/18/88 - Feher
5,125,238 - 06/30/92 - Ragan, et al.
5,300,102 - 04/05/94 - Augustine, et al.
5,324,320 - 06/28/94 - Augustine, et al.
5,350,417 - 09/27/94 - Augustine, et al.
5,405,371 - 04/11/95 - Augustine, et al.
5,785,723 - 07/28/98 - Beran, et al.

Signed and Sealed this

Twenty-ninth Day of January, 2002

*Attest:*

*Attesting Officer*

JAMES E. ROGAN
*Director of the United States Patent and Trademark Office*